(12) United States Patent  
Akagane

(10) Patent No.: US 8,905,935 B2  
(45) Date of Patent: Dec. 9, 2014

(54) ULTRASONIC SURGICAL APPARATUS

(71) Applicant: Olympus Medical Systems Corp., Tokyo (JP)

(72) Inventor: Tsunetaka Akagane, Hachioji (JP)

(73) Assignee: Olympus Medical Systems Corp., Tokyo (JP)

( * ) Notice: Subject to any disclaimer, the term of this patent is extended or adjusted under 35 U.S.C. 154(b) by 0 days.

(21) Appl. No.: 14/145,379

(22) Filed: Dec. 31, 2013

(65) Prior Publication Data

US 2014/0188014 A1  Jul. 3, 2014

Related U.S. Application Data

(63) Continuation of application No. PCT/JP2013/065717, filed on Jun. 6, 2013.

(60) Provisional application No. 61/656,143, filed on Jun. 6, 2012.

(51) Int. Cl.
*A61B 8/00* (2006.01)
*A61N 7/00* (2006.01)
*A61B 18/00* (2006.01)

(52) U.S. Cl.
CPC .. *A61N 7/00* (2013.01); *A61B 18/00* (2013.01)
USPC ........... 600/459; 600/407; 600/437; 600/443; 601/2

(58) Field of Classification Search
USPC .............. 600/407, 437, 459, 441, 443; 601/2
See application file for complete search history.

(56) References Cited

U.S. PATENT DOCUMENTS

| 5,454,373 A | 10/1995 | Koger et al. |
| 8,348,967 B2 * | 1/2013 | Stulen .......................... 606/169 |
| 2004/0127925 A1 | 7/2004 | Du et al. |
| 2004/0199193 A1 | 10/2004 | Hayashi et al. |
| 2009/0030438 A1 | 1/2009 | Stulen |
| 2009/0030439 A1 | 1/2009 | Stulen |

FOREIGN PATENT DOCUMENTS

| JP | A-10-502849 | 3/1998 |
| JP | A-2000-23994 | 1/2000 |
| JP | A-2004-305441 | 11/2004 |
| JP | A-2006-512149 | 4/2006 |
| JP | A-2010-534523 | 11/2010 |

OTHER PUBLICATIONS

Sep. 10, 2013 International Search Report issued in International Patent Application No. PCT/JP2013/065717 (with translation).

* cited by examiner

*Primary Examiner* — Joel Lamprecht
(74) *Attorney, Agent, or Firm* — Oliff PLC

(57) ABSTRACT

A treatment portion includes a treatment region which treats a treatment part with a liquid which has flowed out from a distal end opening portion and with ultrasonic vibrations while the treatment region is in abutment with the treatment part. The treatment portion further includes a hydrophilic region which is formed by the application of a hydrophilic coat and which is provided in part of the circumferential surface of the treatment portion to be provided from the treatment region to an end portion of the treatment portion located in the distal end opening portion in a longitudinal axis direction.

4 Claims, 8 Drawing Sheets

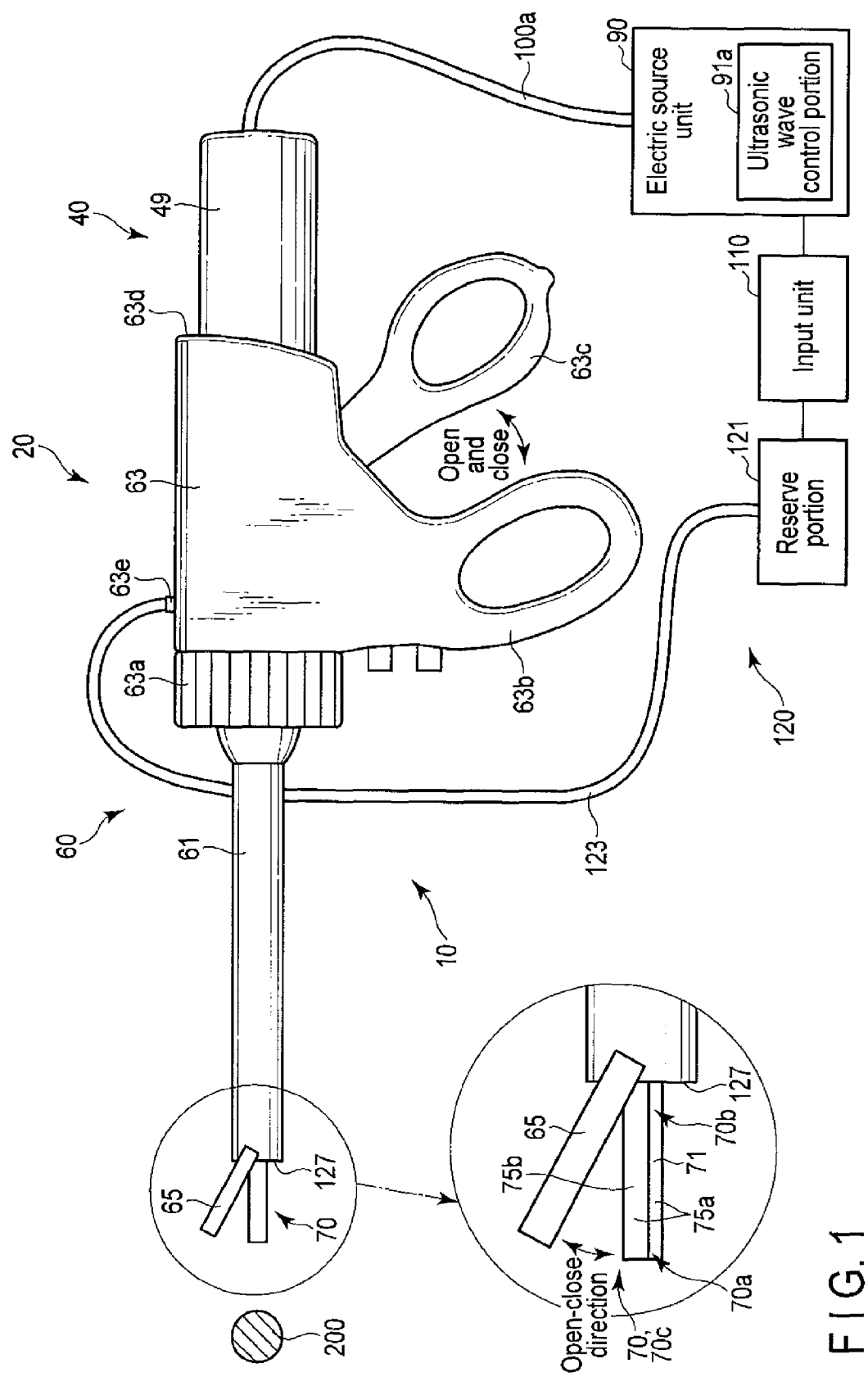
F I G. 1

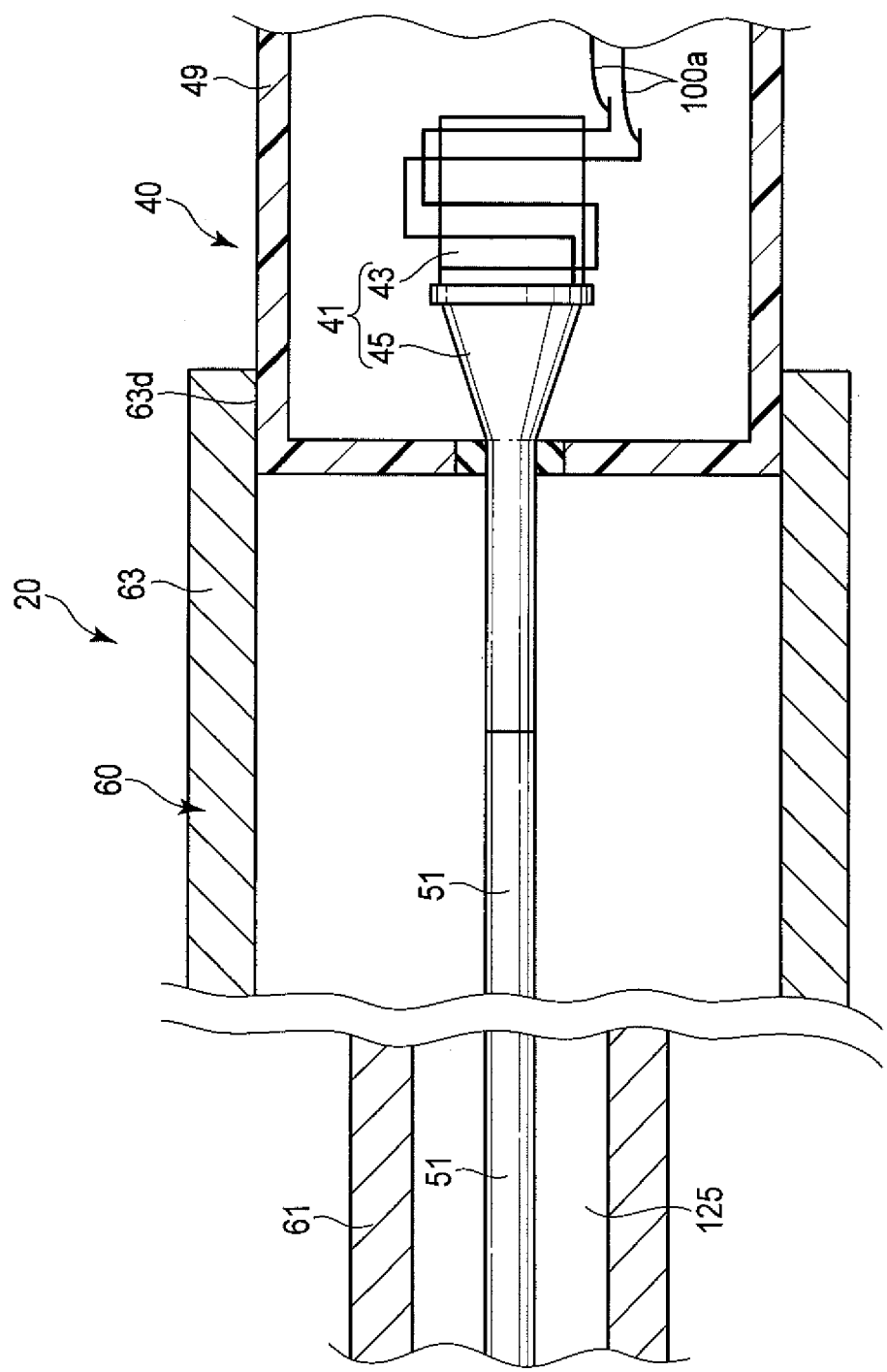
F I G. 2

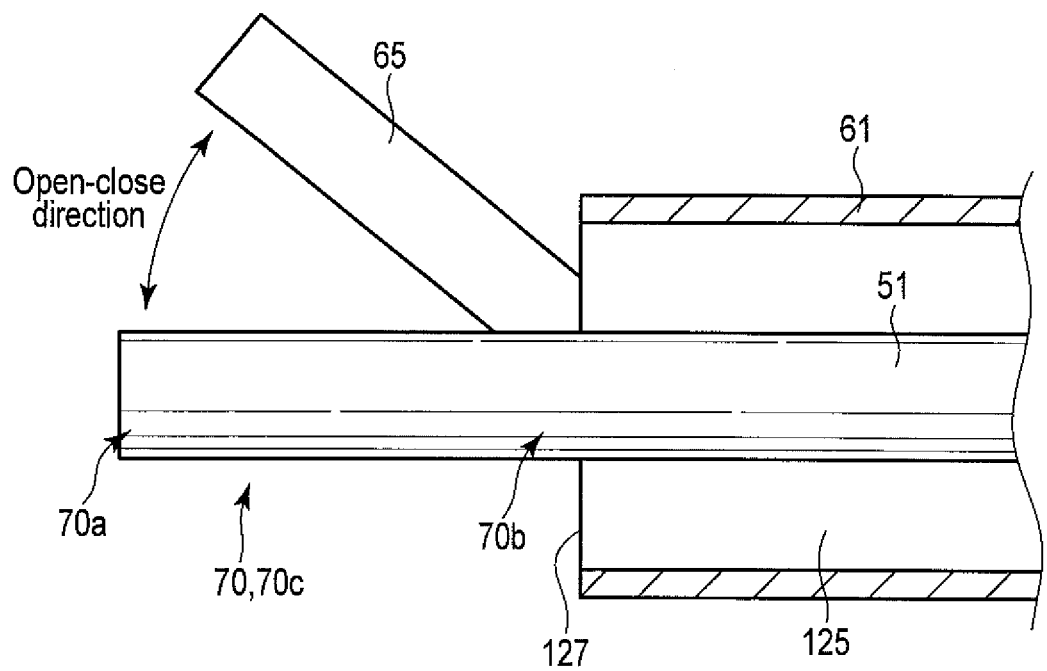
F I G. 3

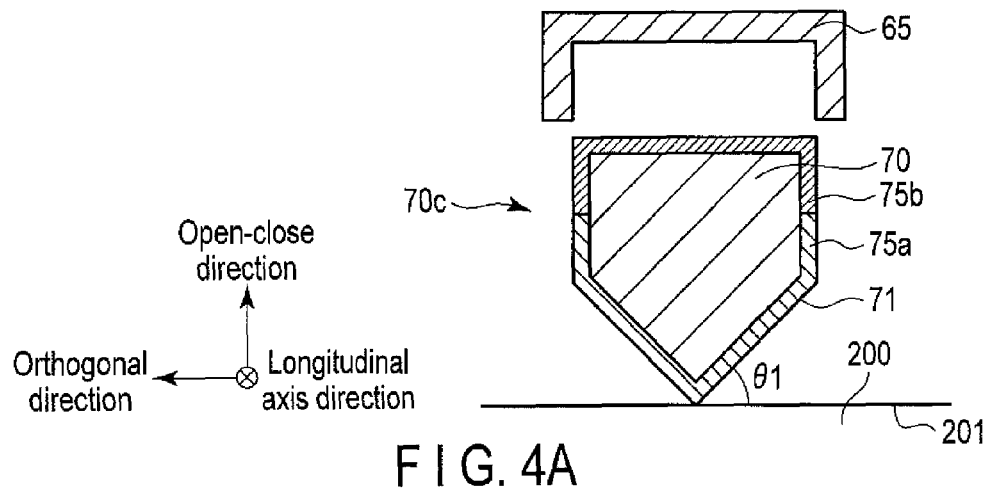
F I G. 4A
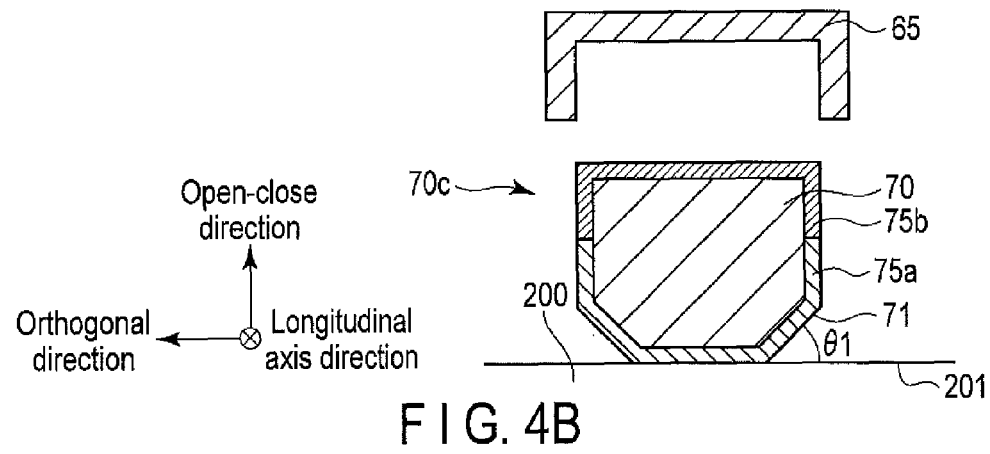
F I G. 4B
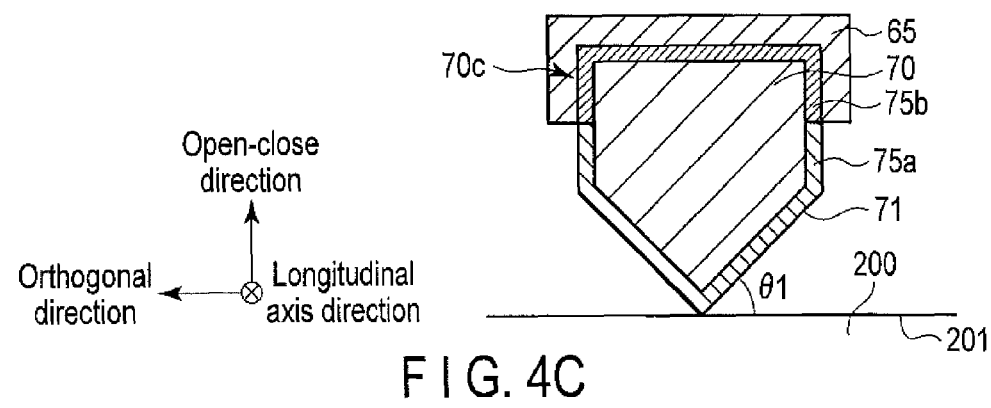
F I G. 4C

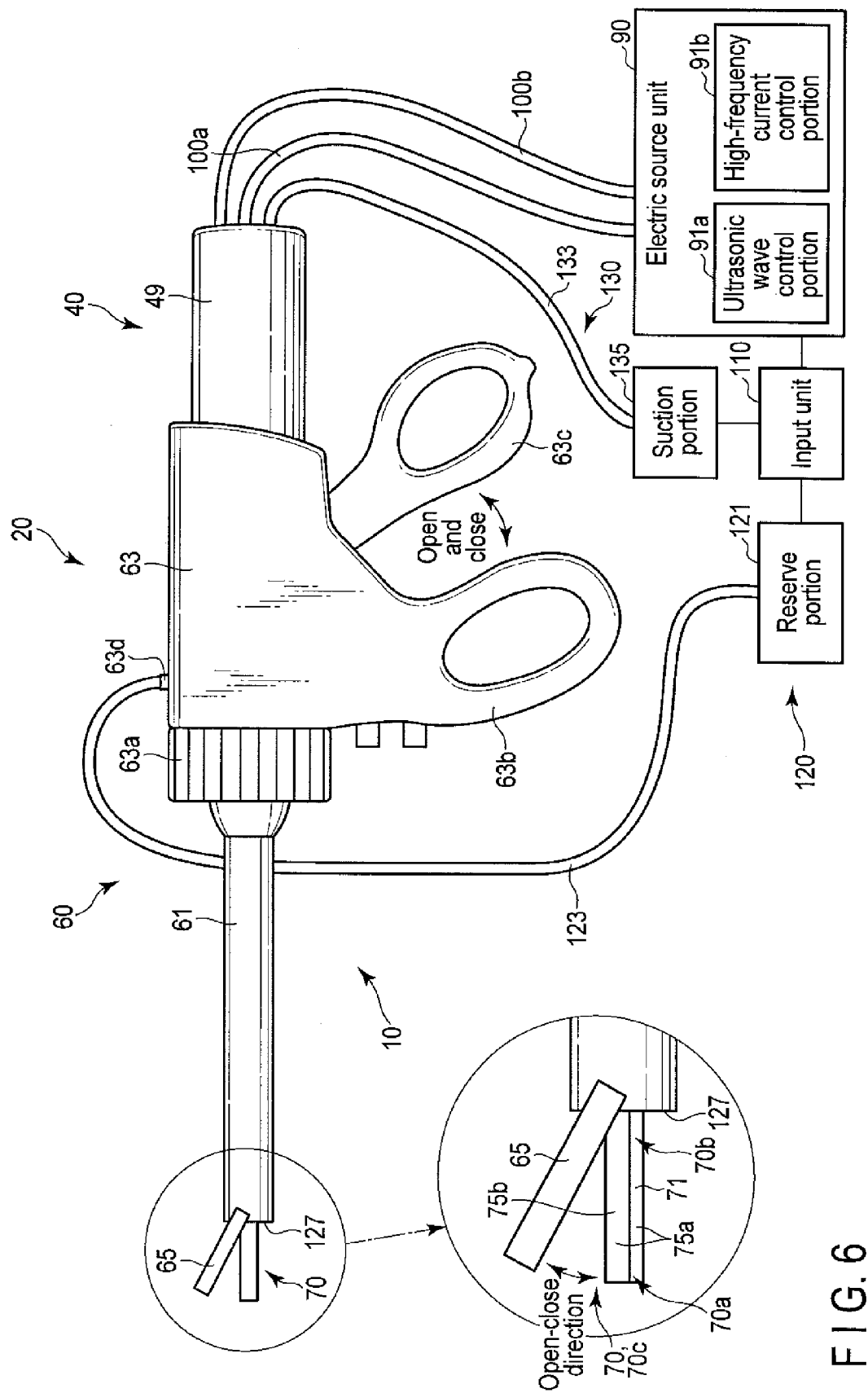
F I G. 6

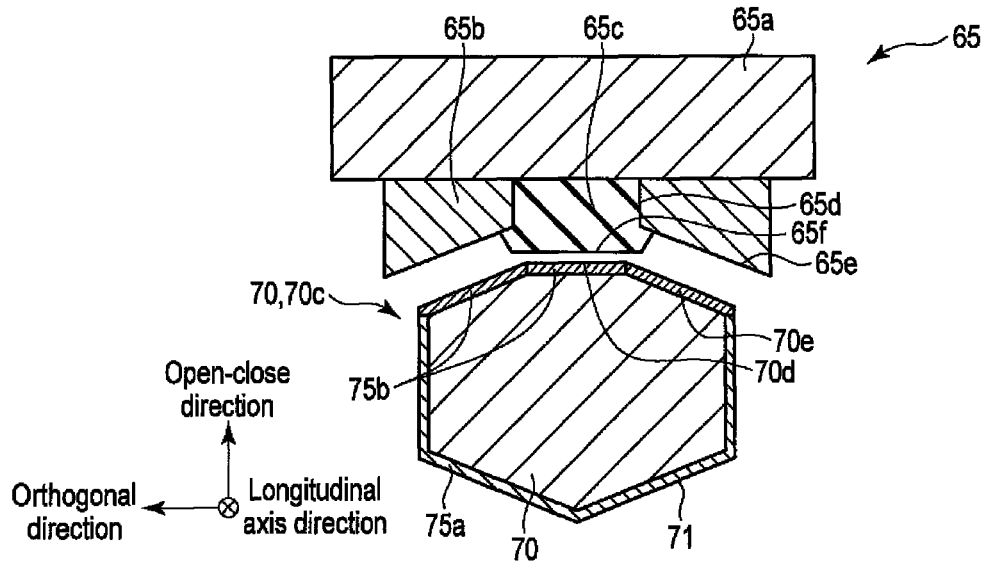
F I G. 7
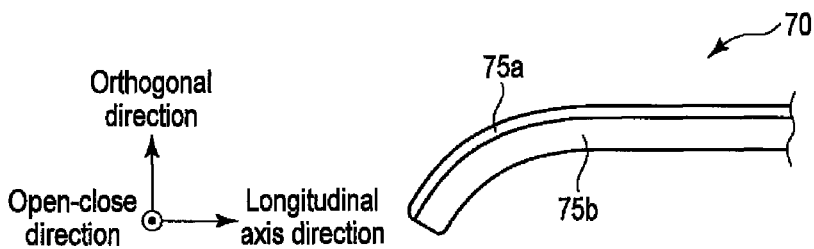
F I G. 8A
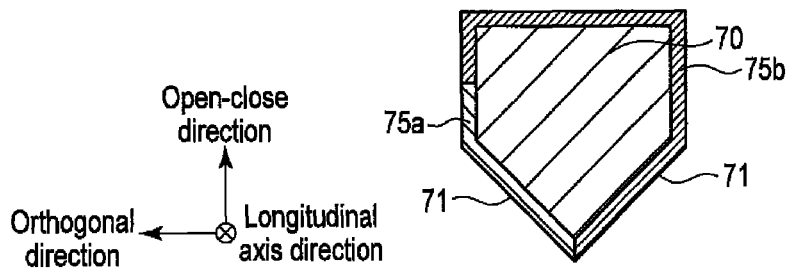
F I G. 8B

ULTRASONIC SURGICAL APPARATUS

CROSS-REFERENCE TO RELATED APPLICATIONS

This application is a Continuation Application of PCT Application No. PCT/JP2013/065717, filed Jun. 6, 2013 and based upon and claiming the benefit of U.S. Provisional Application No. 61/656,143, filed Jun. 6, 2012, the entire contents of all of which are incorporated herein by reference.

BACKGROUND OF THE INVENTION

1. Field of the Invention

The present invention relates to an ultrasonic surgical apparatus for treatment with ultrasonic vibrations.

2. Description of the Related Art

For example, Jpn. Pat. Appln. KOKAI Publication No. 2000-23994 has disclosed an ultrasonic surgical apparatus. This ultrasonic surgical apparatus includes an ultrasonic vibrator which generates ultrasonic vibrations, and a probe which a treatment portion formed at a distal end portion of the probe, which is connected to the ultrasonic vibrator and which uses the treatment portion to treat a living tissue in a treatment part. The ultrasonic surgical apparatus further includes a sheath which covers parts except for the distal end portion (treatment portion) of the probe, and a grasp member which is disposed at the distal end portion of the sheath and which opens and closes relative to the treatment portion to grasp the living tissue in the treatment part together with the treatment portion.

The ultrasonic surgical apparatus is configured to be able to supply a liquid such as physiological saline to the treatment portion of the probe from the distal end portion of the sheath via a water supply channel formed between the probe and the sheath.

In this ultrasonic surgical apparatus, cavitation is caused by the ultrasonic vibrations of the treatment portion and by the supply of the liquid to the distal end portion (treatment portion) of the probe, so that the living tissue in the treatment part can be ultrasonically treated.

BRIEF SUMMARY OF THE INVENTION

An aspect of an ultrasonic surgical apparatus according to the present invention includes an ultrasonic vibrator which generates ultrasonic vibrations, an ultrasonic probe which has a distal end portion and a proximal end portion and which is connected to the ultrasonic vibrator and which transmits the ultrasonic vibrations generated in the ultrasonic vibrator from the proximal end portion to the distal end portion in a longitudinal axis direction of the ultrasonic probe, a sheath unit into which the ultrasonic probe is inserted, a water supply channel which is provided inside the sheath unit and between the ultrasonic probe and the sheath unit and provided along the longitudinal axis of the ultrasonic probe and through which a liquid flows, a distal end opening portion which is provided at the distal end portion of the sheath unit to allow the liquid which has flowed through the water supply channel to flow out, and a treatment portion which is provided at the distal end portion of the ultrasonic probe to protrude outward from the distal end opening portion, which transmits the ultrasonic vibrations transmitted by the ultrasonic probe to a treatment part, and which treats the treatment part with the ultrasonic vibrations, wherein the treatment portion includes a treatment region which treats the treatment part with the liquid which has flowed out from the distal end opening portion and with the ultrasonic vibrations while the treatment region is in abutment with the treatment part, and a hydrophilic region which is formed by the application of a hydrophilic coat and which is provided in part of the circumferential surface of the treatment portion to be provided from the treatment region to an end portion of the treatment portion located in the distal end opening portion in the longitudinal axis direction.

Advantages of the invention will be set forth in the description which follows, and in part will be obvious from the description, or may be learned by practice of the invention. Advantages of the invention may be realized and obtained by means of the instrumentalities and combinations particularly pointed out hereinafter.

BRIEF DESCRIPTION OF THE SEVERAL VIEWS OF THE DRAWING

The accompanying drawings, which are incorporated in and constitute a part of the specification, illustrate embodiments of the invention, and together with the general description given above and the detailed description of the embodiments given below, serve to explain the principles of the invention.

FIG. 1 is a schematic diagram of an ultrasonic surgical system in a first embodiment according to the present invention;

FIG. 2 is a schematic diagram showing the configuration of an ultrasonic surgical apparatus;

FIG. 3 is a schematic diagram showing the configuration of a distal end portion of a water supply channel;

FIG. 4A is an example of cross-sectional views of a grasp member and a treatment portion that are open;

FIG. 4B is an example of cross-sectional views of the grasp member and the treatment portion that are open;

FIG. 4C is an example of cross-sectional views of the grasp member and the treatment portion that are closed from the state shown in FIG. 4A;

FIG. 6 is a schematic diagram of an ultrasonic surgical system in first and fourth modifications of the first embodiment;

FIG. 7 is an example of cross-sectional views of the grasp member and the treatment portion in the first modification;

FIG. 8A is a top view showing the shape of the treatment portion in a second modification;

FIG. 8B is a cross-sectional view showing the shape of the treatment portion in the second modification.

DETAILED DESCRIPTION OF THE INVENTION

Figure 5A:
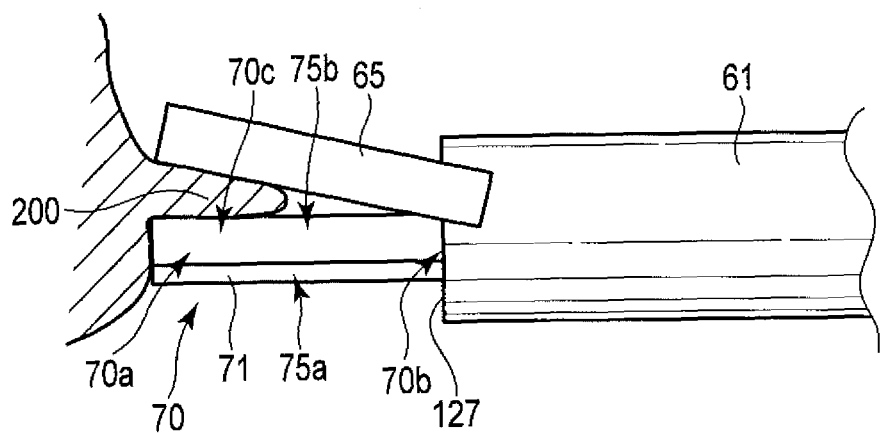
FIG. 5A is a diagram showing how a treatment part grasped by the grasp member and the treatment portion is treated with ultrasonic vibrations.

Hereinafter, embodiments of the present invention will be described in detail with reference to the drawings.

[First Embodiment]

[Configuration]

The first embodiment is described with reference to FIG. 1, FIG. 2, FIG. 3, FIG. 4A, FIG. 4B, FIG. 4C, FIG. 5A, and FIG. 5B. In some of the drawings, some components are not shown for clarity.

[Ultrasonic Surgical System (Hereinafter, Surgical System 10)]

As shown in FIG. 1, the surgical system 10 includes an ultrasonic surgical apparatus (hereinafter, surgical apparatus 20) which treats a treatment part 200 such as a living tissue with ultrasonic vibrations, and an electric source unit 90 which generates an electric current for the ultrasonic vibration of the surgical apparatus 20. The surgical system 10 further includes a cable 100a which has one end connected to the surgical apparatus 20 and the other end connected to the electric source unit 90 to supply the electric current generated in the electric source unit 90 to the surgical apparatus 20 from the electric source unit 90, and an input unit 110 such as a foot switch, and a water supply unit 120.

[Surgical Apparatus 20]

As shown in FIG. 1, FIG. 2, and FIG. 3, the surgical apparatus 20 includes an ultrasonic vibrator unit (hereinafter, vibrator unit 40) which generates ultrasonic vibrations by the electric current supplied from the electric source unit 90 via the cable 100a, and an ultrasonic probe (hereinafter, probe 51) which is connected to the vibrator unit 40 and which is a transmission member to transmit the ultrasonic vibrations generated in the vibrator unit 40. The surgical apparatus 20 further includes a sheath unit 60 into which the probe 51 is inserted, and a treatment portion 70 which is provided at the distal end portion of the probe 51 and which transmits, to the treatment part 200, the ultrasonic vibrations transmitted by the probe 51 and which treats the treatment part 200 with the ultrasonic vibrations.

[Vibrator Unit 40]

As shown in FIG. 1 and FIG. 2, the vibrator unit 40 includes an ultrasonic vibrator (hereinafter, vibrator 41) which generates ultrasonic vibrations, and a case 49 which houses the vibrator 41.

As shown in FIG. 2, the vibrator 41 includes a piezoelectric element 43 which converts the electric current supplied from the electric source unit 90 to ultrasonic vibrations, and a horn 45 which amplifies the amplitude of the ultrasonic vibrations generated in the piezoelectric element 43.

As shown in FIG. 2, the piezoelectric element 43 has, for example, a ring-shape, and more than one piezoelectric element 43 is provided. The piezoelectric elements 43 are in close contact with one another along the longitudinal axis direction of the vibrator 41. The piezoelectric element 43 provided at the distal end portion of the vibrator 41 is connected to the horn 45. The piezoelectric element 43 is connected to the cable 100a.

As shown in FIG. 2, the horn 45 has, for example, a columnar shape. The horn 45 is attached to the case 49 so that a distal end portion of the horn 45 protrudes from the case 49. The horn 45 is an amplitude increasing portion which increases the amplitude of ultrasonic vibrations.

This vibrator 41 is, for example, a bolt-clamped Langevin type transducer (BLT).

[Probe 51]

As shown in FIG. 2, the probe 51 is formed by an elongated member having a longitudinal axis. This probe 51 has the same thickness as, for example, that of the distal end portion of the horn 45. As shown in FIG. 2, the probe 51 includes a proximal end portion connected to the distal end portion of the horn 45 (the distal end portion of the vibrator 41), and a distal end portion functioning as a treatment portion 70 which transmits ultrasonic vibrations to the treatment part 200 as shown in FIG. 3. The ultrasonic vibrations are transmitted to the proximal end portion from the vibrator 41. The ultrasonic vibrations are then transmitted to the distal end portion side of the probe 51 from the proximal end portion of the probe 51.

[Sheath Unit 60]

As shown in FIG. 1 and FIG. 2, the sheath unit 60 includes a sheath 61 through which the probe 51 is inserted, and a holding portion 63 which is provided between the case 49 and the sheath 61 and which is coupled to the case 49 and which holds the sheath 61.

The sheath 61 has, for example, a cylindrical shape. The sheath 61 includes a proximal end portion connected to the holding portion 63 as shown in FIG. 1, a distal end portion from which the treatment portion 70 serving as the distal end portion of the probe 51 protrudes as shown in FIG. 1 and FIG. 3, and a grasp member 65 provided at the distal end portion of the sheath 61 as shown in FIG. 1 and FIG. 3.

The grasp member 65 is capable of opening and closing relative to the treatment portion 70 in an open-close direction that intersects at right angles with the longitudinal axis direction of the probe 51. As shown in FIG. 3 and FIG. 5A, when the grasp member 65 is closed, the grasp member 65 hold the treatment part 200 together with the treatment portion 70 to grasp the treatment part 200 together with the treatment portion 70. A distal grasp portion is formed by the treatment portion 70 and the grasp member 65.

As shown in FIG. 1 and FIG. 2, the holding portion 63 includes a rotational operation knob 63a which is provided at the distal end portion of the holding portion 63 and which is coupled to the sheath 61, a fixed handle 63b, a movable handle 63c capable of opening and closing relative to the fixed handle 63b, and an opening portion 63d which is provided at the proximal end portion of the holding portion 63 and which is coupled to the case 49.

The rotational operation knob 63a is rotatable around the axis of the probe 51, and can be coupled to the sheath 61. BY the rotational operation knob 63a coupled to the sheath 61 rotates, the sheath 61 rotates around the axis relative to the probe 51 together with the rotational operation knob 63a.

The movable handle 63c is attached to the holding portion 63 so that the movable handle 63c is opened and closed relative to the fixed handle 63b. The movable handle 63c is coupled to the grasp member 65 by an unshown transmission member. This transmission member has a function to transmit an open-close force of the movable handle 63c to the grasp member 65. Thus, if the movable handle 63c is opened and closed relative to the fixed handle 63b, the grasp member 65 is opened and closed relative to the treatment portion 70 by the transmission member. The holding portion 63 has a function of a handle unit to be grasped by a surgeon.

[Electric Source Unit 90]

The electric source unit 90 includes an ultrasonic wave control portion 91a which is connected to the input unit 110 and which controls the electric current for ultrasonic vibrations in accordance with an input amount of the input unit 110.

[Water Supply Unit 120]

As shown in FIG. 1, the water supply unit 120 includes a reserve portion 121 which is provided outside the surgical apparatus 20 and which reserves a liquid such as physiological saline, and a water supply tube 123 which supplies the liquid reserved in the reserve portion 121. As shown in FIG. 2 and FIG. 3, the water supply unit 120 also includes a water supply channel 125 which is formed inside the holding portion 63 and between the sheath 61 and the probe 51 and through which the liquid supplied from the water supply tube 123 flows, and a distal end opening portion 127 which id provided at the distal end portion of the sheath 61 to allow the liquid which has flowed through the water supply channel 125 to flow out. The water supply unit 120 is provided, for example, along the longitudinal axis of the probe 51. The treatment portion 70 protrudes outward from the distal end opening portion 127.

The reserve portion 121 is connected to the input unit 110. The reserve portion 121 controls the supply amount of the liquid in accordance with the input amount of the input unit 110.

As shown in FIG. 1, the water supply tube 123 is attached to, for example, a water supply cap 63e provided in the holding portion 63.

As shown in FIG. 2 and FIG. 3, the water supply channel 125 provided inside the sheath 61 and between the probe 51 and the sheath 61 represents the space between the outer circumferential surface of the probe 51 and the inner circumferential surface of the sheath 61 in the diametrical direction of the sheath 61. The water supply channel 125 is covered with the sheath 61.

Therefore, as shown in FIG. 3, the distal end opening portion 127 represents the distal end portion of the sheath 61 which is in communication with the outside.

Thus, the water supply unit 120 supplies the liquid reserved in the reserve portion 121 to the surgical apparatus 20 via the water supply tube 123. The supplied liquid then flows out from the distal end portion of the sheath 61 (the distal end opening portion 127) through the water supply channel 125 formed between the sheath 61 and the probe 51 of the surgical apparatus 20.

The liquid is also supplied, for example, to check a bleeding part and to wash the inside of a body cavity. In ultrasonic treatment, ultrasonic vibrations are transmitted to the distal end of the probe 51. In this case, cavitation is generated in the liquid supplied by the water supply tube 123. The treatment part 200 having low elasticity, for example, a hepatic cell is selectively shattered and emulsified by the cavitation. In this case, the treatment part 200 having high elasticity, for example, a blood vessel is not shattered by the cavitation.

[Treatment Portion 70]

As shown in FIG. 1, the treatment portion 70 has a linear shape. The treatment portion 70 includes the distal end portion of the probe 51 which ultrasonically vibrates. Thus, as shown in FIG. 3, the treatment portion 70 is provided at the distal end portion of the probe 51 to protrude outward from the distal end opening portion 127 (the distal end portion of the sheath 61). The treatment portion 70 includes a distal end portion 70a shown in FIG. 3, a proximal end portion 70b which represents a root of the treatment portion 70 protruding from the sheath 61 (the distal end opening portion 127) as shown in FIG. 3, and a treatment region 70c which treats the treatment part 200 while the treatment region 70c is in abutment with the treatment part 200 as shown in FIG. 5A and FIG. 5J.

[Treatment Region 70c]

The treatment region 70c represents the entire circumferential surface of the treatment portion 70 including the distal end portion 70a and the proximal end portion 70b.

For example, when the treatment portion 70 treats the treatment part 200 with ultrasonic vibrations while grasping the treatment part 200 together with the grasp member 65 as shown in FIG. 5A, the treatment region 70O represents a region located on the upper surface of the treatment portion 70 facing the grasp member 65. This upper surface represents, in the open-close direction, the surface in the close direction, i.e., the surface on the side of the grasp member 65. More specifically, the treatment region 70c represents a region which is covered with the grasp member 65 and faces the grasp member 65 when the grasp member 65 is closed. That is, the treatment region 70c represents an uncoated region 75b described later.

The open direction of the treatment portion 70 represents the side of the treatment portion 70 which faces and comes closer to the treatment part 200. The close direction of the treatment portion 70 represents the side of the treatment portion 70 which faces and comes closer to the grasp member 65.

Figure 5B:
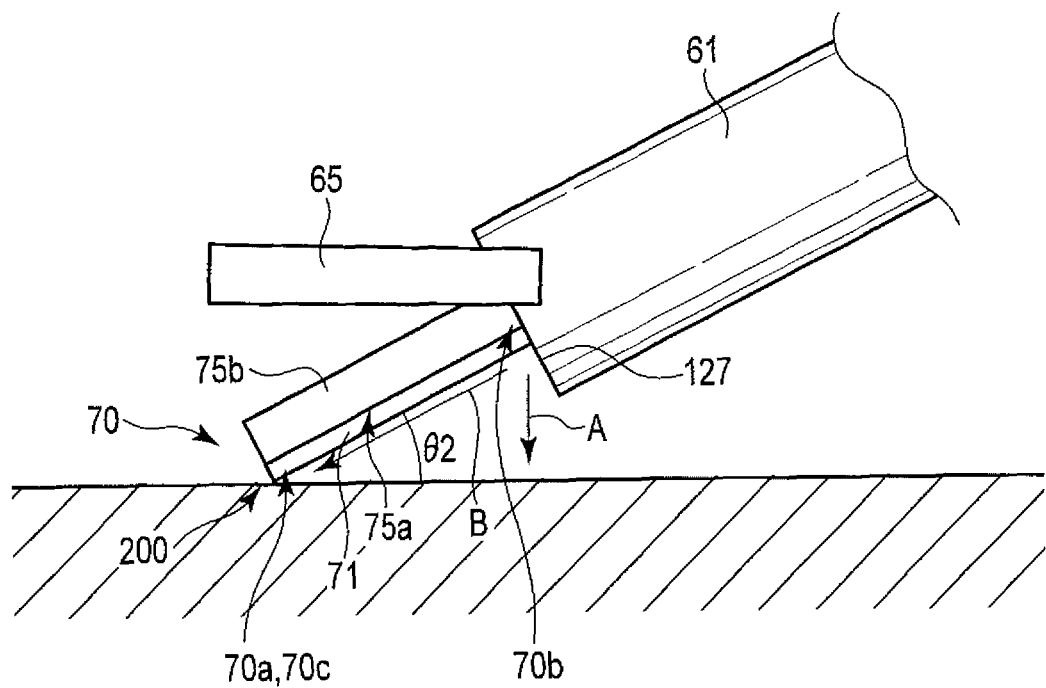
FIG. 5B is a diagram showing how the treatment part which is in abutment with the treatment portion is treated with a liquid and ultrasonic vibrations, and showing the flow of the liquid from a distal end opening portion.

For example, as shown in FIG. 5B, when the treatment portion 70 treats the treatment part 200 with the liquid flowing out from the distal end opening portion 127 and with ultrasonic vibrations, the treatment region 70c represents a region which faces, for example, the treatment part 200 and which is located on the lower surface of the distal end portion 70a abutting on the treatment part 200 as shown in FIG. 5B. This lower surface represents, in the open-close direction, the surface in the open direction, i.e., the surface on the side of the treatment part 200. More specifically, the treatment region 70c represents a hydrophilic region 75a described later.

[Inclined Plane 71]

As shown in FIG. 4A and FIG. 4B, a direction that intersects at right angles with the longitudinal axis direction of the treatment portion 70 and the open-close direction is refereed to as an orthogonal direction. As shown in FIG. 4A and FIG. 4B, the treatment portion 70 is tapered in its cross-sectional shape showing a plane direction formed in the open-close direction and the orthogonal direction. More specifically, the treatment portion 70 is tapered off from the grasp member 65 in the open-close direction. In other words, the treatment portion 70 faces the treatment part 200 in the open-close direction, and is tapered from the side of the grasp member 65 to the side of the treatment part 200. Thus, the treatment portion 70 has the inclined plane 71 which is inclined relative to the orthogonal direction (open-close direction). The inclined plane 71 is a counter surface which faces the treatment part 200. The inclined plane 71 does not face the grasp member 65. In the open-close direction, the inclined plane 71 represents the lower surface of the treatment portion 70, i.e., the surface of the treatment portion 70 on the side of the open direction. In the open-close direction, the inclined plane 71 is provided between a plane in the orthogonal direction and the longitudinal axis direction where the central axis of the treatment portion 70 is provided, and the treatment part 200.

As shown in FIG. 4A, FIG. 4B, and FIG. 4C, an angle formed between a plane 201 which faces the inclined plane 71 and which includes the orthogonal direction and the longitudinal axis direction, and the inclined plane 71 is referred to as an inclination angle θ1. When the lower surface of the probe 51 (treatment portion 70) is only composed of a surface having a large inclination angle θ1, the surface in which the liquid and the probe 51 contact each other is significantly reduced because the liquid concentrates in the sharp distal end portion. Therefore, the liquid which has flowed out from the distal end opening portion 127 as shown in FIG. 5J easily drops by its weight from the proximal end portion 70b in the open direction (downward) as indicated by an arrow A shown in FIG. 5B. Accordingly, the lower surface is preferably formed to include a plane (horizontal plane) having an inclination angle θ1 of 0 degrees as shown in FIG. 4B, and the inclined plane 71 having an inclination angle θ1 of at least less than 45 degrees, or a smoothly curved surface.

[Hydrophilic Region 75a, Uncoated Region 75b]

As shown in FIG. 1, FIG. 4A, FIG. 4B, FIG. 4C, and FIG. 5B, the treatment portion 70 has the hydrophilic region 75a which is formed by the application of a hydrophilic coat. The hydrophilic coat is resistant to a heat of, for example, 200 degrees or more.

The hydrophilic region 75a prevents the liquid which has flowed out from the distal end opening portion 127 from dropping down by its weight as indicated by the arrow A shown in FIG. 5B, and allows the liquid to drop to the treatment region 70c located on the lower surface of the distal end portion 70a from the distal end opening portion 127 as indicated by an arrow B shown in FIG. 5B. Thus, as shown in FIG. 1 and FIG. 5B, the hydrophilic region 75a is linearly provided from the distal end portion 70a to the proximal end portion 70b located in the distal end opening portion 127 along the longitudinal axis direction of the treatment portion 70. The hydrophilic region 75a is preferably provided up to the probe 51 covered with the sheath 61.

As shown in FIG. 4A, FIG. 4B, and FIG. 4C, the hydrophilic region 75a is provided in at least part of the circumferential surface of the treatment portion 70. More specifically, as shown in FIG. 4A, FIG. 4B, FIG. 4C, and FIG. 5B, the hydrophilic region 75a is provided in the circumferential surface of the treatment portion 70 including the inclined plane 71 and provided in regions except for a region which is covered with the grasp member 65 and faces the grasp member 65 when the grasp member 65 is closed. The hydrophilic region 75a has only to be provided in the counter surface which faces the treatment part 200 in the circumferential surface of the treatment portion 70 so that the hydrophilic region 75a is provided in the inclined plane 71. The hydrophilic region 75a is included in the treatment region 70c.

That is, as shown in FIG. 4A, FIG. 4B, and FIG. 4C, the treatment portion 70 includes the hydrophilic region 75a (coated region), and the uncoated region 75b which is not coated with the hydrophilic coat. The uncoated region 75b is the region which is covered with the grasp member 65 and faces the grasp member 65 when the grasp member 65 is closed, the region which the grasp member 65 is fitted to the treatment portion 70. The uncoated region 75b is a forbidden region where the application of the hydrophilic coat is forbidden. As shown in FIG. 1 and FIG. 5B, the uncoated region 75b is provided from the distal end portion 70a to the proximal end portion 70b along the longitudinal axis direction of the treatment portion 70. As shown in FIG. 4A, FIG. 4B, and FIG. 4C, the uncoated region 75b is in communication with the hydrophilic region 75a in the circumferential direction of the treatment portion 70.

For example, when the hydrophilic region 75a is provided in the uncoated region 75b, the grasp member 65 closes relative to the treatment portion 70 to grasp the treatment part 200 together with the treatment portion 70 as shown in FIG. 5A, and the treatment portion 70 then ultrasonically vibrates. In this situation, the hydrophilic region 75a provided in the uncoated region 75b abuts on the treatment part 200. At the same time, the hydrophilic region 75a ultrasonically vibrates against the treatment part 200 because of the ultrasonic vibrations, rubs against the treatment part 200 because of the ultrasonic vibrations, and is abrases and deteriorates because of heat generated by the friction. The same also applies to the case where the hydrophilic region 75a rubs against the grasp member 65 when the hydrophilic region 75a is in abutment with the grasp member 65 as shown in FIG. 4C. The uncoated region 75b is provided to prevent damage to the hydrophilic region 75a including abrasion and deterioration.

[Function 1]

The movable handle 63c closes relative to the fixed handle 63b, and the grasp member 65 is closed relative to the treatment portion 70 to grasp the treatment part 200 together with the treatment portion 70 as shown in FIG. 5A. At the same time, the treatment region 70c located on the lower surface of the treatment portion 70 facing the grasp member 65 abuts on the treatment part 200.

When the ultrasonic wave control portion 91a controls an electric current in response to the operation of the input unit 110, the vibrator 41 generates ultrasonic vibrations. The ultrasonic vibrations are transmitted to the treatment portion 70 from the vibrator 41 via the probe 51. In this case, the treatment region 70c is in abutment with the treatment part 200, and transmits the ultrasonic vibrations to the treatment part 200 accordingly.

As a result, thermal friction occurs between the treatment portion 70 and the treatment part 200. The treatment part 200 is cut open by the thermal friction. This treatment part 200 represents, for example, a blood vessel having high elasticity.

In this case, the uncoated region 75b is provided, the uncoated region 75b is in abutment with the treatment part 200, and the hydrophilic region 75a is not in abutment with the treatment part 200. Therefore, the uncoated region 75b prevents damage to the hydrophilic region 75a including abrasion and deterioration caused by the ultrasonic vibrations.

[Function 2]

For example, when the input unit 110 is operated, the reserve portion 121 supplies the liquid to the water supply tube 123. The liquid is supplied, for example, simultaneously with the generation of ultrasonic vibrations by the vibrator 41. As a result, the liquid flows from the water supply tube 123 to the water supply channel 125, and flows out from the distal end opening portion 127.

At the same time, as shown in FIG. 5B, the treatment region 70c located on the lower surface of the distal end portion 70a facing the treatment part 200 abuts on the treatment part 200.

In this case, as indicated by the arrow B shown in FIG. 5B, in the treatment portion 70, the liquid drops to the treatment region 70c located on the lower surface of the distal end portion 70a from the distal end opening portion 127 because of the hydrophilic region 75a. At the same time, the liquid does not easily drop down from the proximal end portion 70b as indicated by the arrow A shown in FIG. 5B because of the inclined plane 71, and is urged to drop to the treatment region 70c located on the lower surface of the distal end portion 70a from the distal end opening portion 127 as indicated by the arrow B shown in FIG. 5B.

This ensures that the liquid flows to the distal end portion 70a without being influenced by an inclination angle θ2 of the treatment portion 70 relative to the treatment part 200, the protrusion amount of the treatment portion 70 protruding from the distal end opening portion 127, and the distance between the distal end portion 70a and the distal end opening portion 127. The liquid flows from the treatment region 70c located on the lower surface of the distal end portion 70a to the treatment part 200 with which the treatment region 70c is in abutment.

Cavitation is then generated in the liquid. The treatment part 200 is selectively shattered and emulsified by the cavitation. This treatment part 200 represents, for example, a hepatic cell having low elasticity.

[Advantageous Effects]

As described above, according to the present embodiment, the hydrophilic region 75a ensures that the liquid can flow to the treatment region 70c without being influenced by the inclination angle θ2 of the treatment portion 70 relative to the treatment part 200, the protrusion amount of the treatment portion 70 protruding from the distal end opening portion 127, and the distance between the distal end portion 70a and the distal end opening portion 127. This treatment region 70c is located on the lower surface of the distal end portion 70a facing the treatment part 200. Therefore, according to the present embodiment, the liquid can flow from the treatment region 70c located on the lower surface of the distal end portion 70a to the treatment part 200 with which the treatment region 70c is in abutment, which makes it possible to prevent any hindrance to the treatment that uses the ultrasonic vibrations.

According to the present embodiment, the uncoated region 75b can prevent the hydrophilic region 75a from being damaged by ultrasonic vibrations.

According to the present embodiment, the inclined plane 71 can urge the liquid to drop to the treatment region 70c located on the lower surface of the distal end portion 70a from the distal end opening portion 127. Moreover, according to the present embodiment, the hydrophilic region 75a is provided from the distal end portion 70a to the proximal end portion 70b along the longitudinal axis direction of the treatment portion 70.

The hydrophilic region 75a is also provided in the circumferential surface of the treatment portion 70 including the inclined plane 71. According to the present embodiment, this ensures that the liquid can flow to the treatment region 70c located on the lower surface of the distal end portion 70a as indicated by the arrow B shown in FIG. 5B, and can flow from the treatment region 70c located on the lower surface of the distal end portion 70a to the treatment part 200 with which the treatment region 70c is in abutment. According to the present embodiment, the inclined plane 71 is provided on the lower surface of the treatment portion 70, so that the liquid can quickly flow to the treatment part 200.

[Modification 1 - High-Frequency Treatment - FIG. 6, FIG. 7]

[Configuration]

In the present modification, the surgical apparatus 20 may conduct treatment with a high-frequency current as shown in FIG. 6.

[Electric Source Unit 90]

As shown in FIG. 6, the electric source unit 90 further includes a high-frequency current control portion 91b which is connected to the input unit 110 and which controls an electric current for high-frequency waves in accordance with the input amount of the input unit 110. The high-frequency current control portion 91b is connected to one end of a cable 100b. The other end of the cable 100b is connected to the case 49 and further connected to the vibrator 41. In this way, electric paths for high-frequency treatment are respectively formed from the electric source unit 90 to the grasp member 65 and the treatment portion 70 via the cable 100a, the vibrator unit 40, the probe 51, and the sheath 61.

[Grasp Member 65]

As shown in FIG. 7, the grasp member 65 includes a grasp body 65a, an electrode member 65b provided in the grasp body 65a, and a pad member 65c provided in the electrode member 65b.

[Grasp Body 65a]

The grasp body 65a is made of a rigid and electrically conductive material. The grasp body 65a is provide at the distal end portion of the sheath 61 to open and close relative to the treatment portion 70 in response to the opening and closing of the movable handle 63c.

[Electrode Member 65b]

The electrode member 65b is made of a rigid and electrically conductive material. The electrode member 65b functions as one electrode of a bipolar electrode for high-frequency treatment. The electrode member 65b is provided in the grasp body 65a to face the treatment portion 70. The electrode member 65b has a depression portion 65d depressed from the treatment portion 70 toward the grasp body 65a in the open-close direction. The depression portion 65d is provided along the longitudinal axis direction of the grasp member 65. The depression portion 65d is provided coaxially with the longitudinal axis of the treatment portion 70 in the open-close direction. The depression portion 65d faces a flat abutment portion 70d provided on the upper surface of the treatment portion 70. The upper surface of the treatment portion 70 represents a surface on the side of the close direction in the open-close direction.

The electrode member 65b has a pair of electrode receiving surfaces 65e provided on both sides of the depression portion 65d in the width direction of the grasp member 65. The electrode receiving surfaces 65e expand in the orthogonal direction (the width direction of the grasp member 65) toward the treatment portion 70 in the open-close direction to cover the upper side of the treatment portion 70. The electrode receiving surfaces 65e are respectively provided parallel to electrode surfaces 70e of the treatment portion 70 formed on both sides of the abutment portion 70d of the treatment portion 70 in the orthogonal direction. When the grasp member 65 is closed relative to the treatment portion 70, a clearance is secured between the electrode portion and the treatment portion 70.

[Pad Member 65c]

As shown in FIG. 7, the pad member 65c is made of an insulating biomaterial softer than the probe 51, for example, polytetrafluoroethylene. The pad member 65c is fitted in the depression portion 65d. Therefore, the pad member 65c faces the abutment portion 70d of the treatment portion 70. The pad member 65c has a flat abutment receiving portion 65f which protrudes from the electrode member 65b toward the treatment portion 70 in the open-close direction and which abuts on the abutment portion 70d of the treatment portion 70 when the grasp member 65 is closed relative to the treatment portion 70. In a section that intersects at right angles with the longitudinal axis direction, the abutment receiving portion 65f has a shape corresponding to the abutment portion 70d of the treatment portion 70. Thus, the pad member 65c is provided in the electrode member 65b to face the abutment portion 70d of the treatment portion 70, and abuts on the treatment portion 70 when the grasp member 65 is closed relative to the treatment portion 70.

[Treatment Portion 70]

The electrode surfaces 70e of the treatment portion 70 function as the other electrode of the bipolar electrode for high-frequency treatment. The electrode surfaces 70e and the abutment portion 70d of the treatment portion 70 also function as the treatment region 70c.

[Hydrophilic Region 75a, Uncoated Region 75b]

In the present modification, the hydrophilic region 75a is provided in the circumferential surface of the treatment portion 70 including the inclined plane 71, and also provided in regions except for a region which is covered with the grasp member 65 and faces the grasp member 65 when the grasp member 65 is closed. In the present modification in particular, the hydrophilic region 75a is provided in the regions of the treatment portion 70 except for the electrode surfaces 70e which function as the other electrode of the bipolar electrode and the abutment portion 70d on which the abutment receiving portion 65f of the pad member 65c abuts.

In this case, the uncoated region 75b is provided in the bipolar electrode of the treatment portion 70, i.e., in the electrode surfaces 70e and in the abutment portion 70d on which the abutment receiving portion 65f abuts.

For example, if the hydrophilic region 75a is provided in the electrode surfaces 70e which represent the uncoated region 75b, the hydrophilic region 75a functions as a resistance, which may affect impedance and deteriorate the function of the high-frequency treatment. The uncoated region 75b is provided to prevent deterioration of the function of the high-frequency treatment.

For example, when the hydrophilic region 75a is provided in the abutment portion 70d which represents the uncoated region 75b, the grasp member 65 (abutment receiving portion 65f) closes relative to the treatment portion 70 to grasp the treatment part 200 together with the treatment portion 70 (abutment portion 70d), and the treatment portion 70 then ultrasonically vibrates. In this situation, the hydrophilic region 75a provided in the uncoated region 75b (abutment portion 70d) abuts on the treatment part 200. At the same time, the hydrophilic region 75a ultrasonically vibrates against the treatment part 200 because of the ultrasonic vibrations, rubs against the treatment part 200 because of the ultrasonic vibrations, and is abrase and deteriorates because of heat generated by the friction. The same also applies in the case where the hydrophilic region 75a rubs against the grasp member 65 (abutment receiving portion 65f). The uncoated region 75b is provided to prevent damage to the hydrophilic region 75a including abrasion and deterioration.

[Function]

Operations associated with the treatment and the water supply in the ultrasonic vibrations are substantially similar to the operations in the first embodiment, and are therefore not described in detail.

In a high-frequency treatment, the movable handle 63c closes relative to the fixed handle 63b, and the grasp member 65 is closed relative to the treatment portion 70. As a result, the grasp member 65 and the treatment region 70c grasp the treatment part 200. At the same time, the treatment region 70c which represents the electrode surfaces 70e and the abutment portion 70d abuts on the treatment part 200.

If the high-frequency current control portion 91b controls an electric current as a result of the operation of the input unit 110, a high-frequency current is applied to the electrode member 65b and the treatment portion 70. Thus, the high-frequency current is passed through the treatment part 200 grasped by the grasp member 65 and the treatment portion 70. Consequently, the treatment part 200 is denatured and coagulated.

[Advantageous Effects]

According to the present modification, advantageous effects similar to the advantageous effects in the first embodiment can also be obtained when the ultrasonic treatment is combined with the high-frequency treatment. According to the present modification, the uncoated region 75b can prevent deterioration of the function of the high-frequency treatment.

[Modification 2- FIG. 8A, FIG. 8B]

As shown in FIG. 8A and FIG. 8B, the treatment portion 70 is curved relative to its longitudinal axis direction, and is asymmetric. In this case, together with the inclined plane 71, the hydrophilic region 75a is preferably only provided in the circumferential surface of the treatment portion 70 which is provided outside in the curving direction.

[Modification 3]

According to the present modification, the treatment portion 70 and the grasp member 65 have a double-door structure capable of opening and closing relative to each other. In this case, the treatment portion 70 and the grasp member 65 are curved relative to the longitudinal axis direction of the treatment portion 70 as in Modification 2, and are asymmetric. In this case, as in Modification 2, the hydrophilic regions 75a are preferably provided in the circumferential surfaces of the treatment portion 70 and the grasp member 65 that are respectively provided outside in the curving direction.

Figure 9:
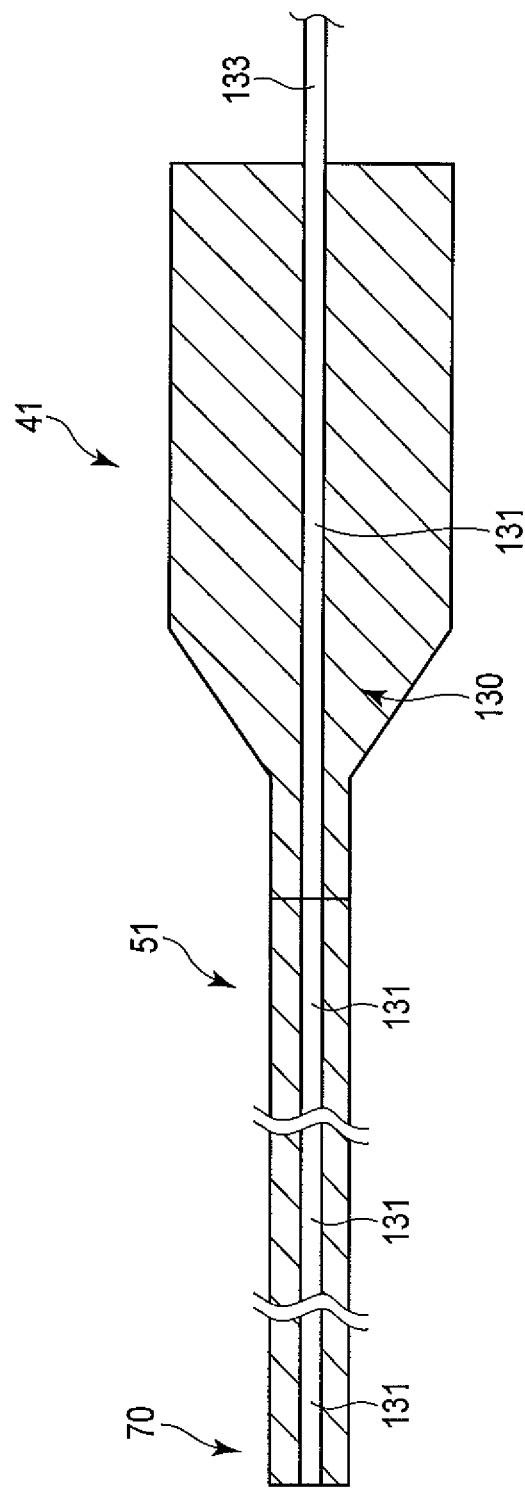
FIG. 9 is a diagram showing a suction unit in the fourth modification.

[Modification 4- Ultrasonic Suction Device - FIG. 6, FIG. 9]

According to the present modification, as shown in FIG. 6 and FIG. 9, the surgical apparatus 20 may perform ultrasonic suction.

In this case, as shown in FIG. 6 and FIG. 9, the surgical system 10 further includes a suction unit 130. As shown in FIG. 6 and FIG. 9, the suction unit 130 includes a cavity 131 which is provided inside the probe 51 including the treatment portion 70 and inside the vibrator 41 and which is provided in the longitudinal axis direction of the probe 51, a suction tube 133 which is provided in the case 49 and which is connected to the proximal end portion of the vibrator 41 to communicate with a proximal end portion of the cavity 131, and a suction portion 135 which sucks the resected treatment part 200 and the liquid via the cavity 131 and the suction tube 133.

A distal end portion of the cavity 131 is provided in the end face of the treatment portion 70, and is open.

The suction portion 135 includes an unshown suction pump which is connected to the input unit 110 and which is driven in accordance with the input unit 110, and an unshown suction bottle which reserves the sucked treatment part 200 and liquid.

According to the present modification, the suction pump is driven by the operation of the input unit 110, and the treatment part 200 resected by the ultrasonic vibrations and the liquid are sucked from the distal end portion of the cavity 131 and discharged into the suction bottle through the cavity 131 and the suction tube 133.

Thus, according to the present modification, the ultrasonic treatment shown in the first embodiment can be combined with the ultrasonic suction treatment.

[Modification 5]

Although the grasp member 65 is provided in the present embodiment, the grasp member 65 may be omitted. In this case, the hydrophilic region 75a has only to be provided in the entire circumferential surface of the treatment portion 70. Thus, according to the present modification, the uncoated region 75b can be omitted, and the hydrophilic region 75a can be easily provided.

[Additional Note 1]

A surgical apparatus including:

an ultrasonic vibrator which generates ultrasonic vibrations;

an ultrasonic probe which is connected to the ultrasonic vibrator and which transmits the ultrasonic vibrations generated in the ultrasonic vibrator;

a sheath unit into which the ultrasonic probe is inserted;

a water supply channel which is provided inside the sheath unit and between the ultrasonic probe and the sheath unit and provided along the longitudinal axis of the ultrasonic probe and through which a liquid flows;

a distal end opening portion provided at the distal end portion of the sheath unit to allow the liquid which has flowed through the water supply channel to flow out;

a treatment portion provided at the distal end portion of the ultrasonic probe to protrude outward from the distal end opening portion, the treatment portion functioning as a bipolar electrode for high-frequency treatment, transmitting the ultrasonic vibrations transmitted by the ultrasonic probe to a treatment part, and treating the treatment part with high-frequency waves and the ultrasonic vibrations; and a grasp member provided at the distal end portion of the sheath unit, the grasp member opening and closing relative to the treatment portion in an open-close direction that intersects at right angles with a longitudinal axis direction of the ultrasonic probe, the grasp member grasping the treatment part together with the treatment portion when closed,
wherein the grasp member includes
a grasp body,
an electrode member which functions as a bipolar electrode for high-frequency treatment and which is provided in the grasp body to face the treatment portion, and
a pad member which is provided in the electrode member to face the treatment portion and which abuts on the treatment portion when the grasp member is closed, and
the treatment portion includes
a treatment region which treats the treatment part with the liquid which has flowed out from the distal end opening portion and with the ultrasonic vibrations while the treatment region is in abutment with the treatment part, the treatment region grasping the treatment part together with the pad member to treat the treatment part with the ultrasonic vibrations when the grasp member is closed, the treatment region treating the treatment part with the high-frequency waves together with the electrode member,
a hydrophilic region which is formed by the application of a hydrophilic coat and which is provided in part of the circumferential surface of the treatment portion to be provided from the treatment region to the end portion of the treatment portion located in the distal end opening portion, and
a forbidden region which faces the electrode member and on which the pad member abuts and where the application of the hydrophilic coat is forbidden.

The present invention is not completely limited to the embodiments described above, and modifications of components can be made at the stage of carrying out the invention without departing from the spirit thereof. Further, various inventions can be made by properly combining the components disclosed in the embodiments described above.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims. and their equivalents.

What is claimed is:

1. An ultrasonic surgical apparatus comprising:
an ultrasonic vibrator which generates ultrasonic vibrations;
an ultrasonic probe which has a distal end portion and a proximal end portion and which is connected to the ultrasonic vibrator and which transmits the ultrasonic vibrations generated in the ultrasonic vibrator from the proximal end portion to the distal end portion in a longitudinal axis direction of the ultrasonic probe;
a sheath unit into which the ultrasonic probe is inserted;
a water supply channel which is provided inside the sheath unit and between the ultrasonic probe and the sheath unit and provided along the longitudinal axis of the ultrasonic probe and through which a liquid flows;
a distal end opening portion which is provided at the distal end portion of the sheath unit to allow the liquid which has flowed through the water supply channel to flow out; and
a treatment portion which is provided at the distal end portion of the ultrasonic probe to protrude outward from the distal end opening portion, which transmits the ultrasonic vibrations transmitted by the ultrasonic probe to a treatment part, and which treats the treatment part with the ultrasonic vibrations,
wherein the treatment portion includes
a treatment region which treats the treatment part with the liquid which has flowed out from the distal end opening portion and with the ultrasonic vibrations while the treatment region is in abutment with the treatment part, and
a hydrophilic region which is formed by the application of a hydrophilic coat and which is provided in part of the circumferential surface of the treatment portion to be provided from the treatment region to an end portion of the treatment portion located in the distal end opening portion in the longitudinal axis direction.

2. The ultrasonic surgical apparatus according to claim 1, wherein the sheath unit includes a grasp member provided at a distal end portion of the sheath unit, the grasp member opening and closing relative to the treatment portion in an open-close direction that intersects at right angles with the longitudinal axis direction of the ultrasonic probe, the grasp member grasping the treatment part together with the treatment portion when closed, and
the treatment portion further includes a forbidden region which is covered with the grasp member when the grasp member is closed, the grasp member being fitted to the treatment portion, the application of the hydrophilic coat being forbidden.

3. The ultrasonic surgical apparatus according to claim 1, wherein the hydrophilic region is provided in a counter surface which faces the treatment part in the circumferential surface of the treatment portion.

4. The ultrasonic surgical apparatus according to claim 1, wherein a probe sectional shape which forms the hydrophilic region is configured to include a curved surface, or a plane having an angle of 45 degrees or more relative to the open-close direction of the grasp member.

* * * * *